United States Patent [19]

Kang

[11] Patent Number: 5,698,533
[45] Date of Patent: Dec. 16, 1997

[54] OPHTHALMIC PHARMACEUTICAL COMPOSITION

[76] Inventor: Meng-Che Kang, 3F, No. 25, Lane 283 Tun Hua N. Rd., Taipei, Taiwan

[21] Appl. No.: 280,827

[22] Filed: Jul. 26, 1994

[51] Int. Cl.⁶ .......................... A61K 31/70; A61K 31/65; A61K 31/43
[52] U.S. Cl. .......................... 514/52; 514/152; 514/198; 514/199; 514/912
[58] Field of Search .......................... 514/52, 152, 198, 514/199, 912

[56] References Cited

PUBLICATIONS

Zimmerman, Annals of Opthalmology, 627–628, 1978.

*Primary Examiner*—Zohreh Fay
*Attorney, Agent, or Firm*—Fish & Richardson P.C.

[57] ABSTRACT

A method of administering a drug to an eye including the steps of: (a) admixing a pharmaceutically acceptable hydrocarbonaceous semi-solid or oil which contains the drug with water at a temperature above the melting point of the semi-solid or oil; and (b) nebulizing the admixture to form liquid drops; and (c) applying the liquid drops to the eye.

9 Claims, No Drawings

OPHTHALMIC PHARMACEUTICAL COMPOSITION

BACKGROUND OF THE INVENTION

The present invention relates to an ophthalmic pharmaceutical composition for use with nebulizers to treat the eyes.

Applying a strong flush of fine drops of a medicated liquid to an eye clearly may cause irritation or even damage to it. Thus, few pharmaceutical compositions for treating the eyes are administered by means of a spray delivery system. While a spray delivery system for applying MISTURA is mentioned in T. J. Zimmerman, Journal of Annals of Ophthalmology, pages 627–628 (May 1978), no technical details are disclosed therein.

Chlorofluorocarbon is commonly used in a spray delivery system as the spray propellant for aerating the liquid to be delivered into fine drops as a strongly ejected flow. As noted above, such a delivery system is clearly unsuitable to be used in eye treatment. Furthermore, chlorofluorocarbon will be banned worldwide after the year 2000.

SUMMARY OF THE INVENTION

It is therefore the principal object of the present invention to provide an ophthalmic pharmaceutical composition which is suitable for use with nebulizers for treating the eyes. It is another object of the present invention to provide an ophthalmic pharmaceutical composition for use with nebulizers for treating the eyes, the composition being presented in the form of a hydrocarbonaceous semi-solid (i.e., a grease, fat or wax-like substance) under room temperature (i.e., about 25° C.). It is still another object of the present invention to provide a spray delivery system for delivering the ophthalmic pharmaceutical composition to the eyes without using the spray propellant chlorofluorocarbon.

One aspect of this invention relates to an ophthalmic pharmaceutical composition comprising: (a) a drug which is 0.01 to 20% (more preferably, 1 to 5% or 0.1 to 10%) by weight, and (b) a pharmaceutically acceptable carrier 80 to 99.99% (more preferably, 90 to 99.9% or 95 to 99%). The carrier is a hydrocarbonaceous semi-solid at room temperature and melts at 30°–100° C. (more preferably, 50°–100° C.).

The drug can be a relief agent for the dry eye syndrome, a nerve-reactivating agent, an astringent agent, an anti-inflammatory agent, an anti-bacterial agent, an anti-fungal agent, an anti-viral agent, an anti-allergic agent, an anti-glaucomatous agent, anti-graft rejection agent, or a cycloplegic agent.

Thus, examples of the drug include hydroxy ethyl cellulose, hydroxy propyl methyl cellulose, gelatin, polyvinyl alcohol, vitamin A, vitamin B1, vitamin B2, vitamin B6, vitamin B12, vitamin C, vitamin E, vitamin K, camphor, menthol, zinc sulfate, naphazoline (e.g., its HCl salt), tetrahydrozoline, phenylephrine, prednisolone acetate, dexamethasone alcohol, sulfanilamide, neomycin, terramycin, erythromycin, gentamicin, amphotericin B, idoxuridine, antazoline, naphazoline, sodium cromoglycate, pilocarpine, epinephrine, timolol, cyclosporine A, tropicamide, and atropine.

Examples of the carrier, on the other hand, include petrolatum and lanolin.

A representative embodiment of the composition of this invention includes petrolatum 88.98% by weight, camphor 9% by weight, menthol 2% by weight, and vitamin B12 0.02% by weight.

If necessary, an emulsifier (e.g., lecithin) can be added to the composition of this invention.

Another aspect of this invention features a method of administering a drug to an eye which is to be treated. The method comprises the steps of: (a) admixing a pharmaceutically acceptable hydrocarbonaceous semi-solid (i.e., in semi-solid form at room temperature) or oil (i.e., in liquid form at room temperature) which contains the drug with water at a temperature above the melting point of the semi-solid or oil; (b) nebulizing the admixture to form liquid drops; and (c) applying the liquid drops to the eye. Examples of the semi-solid or oil include, but are not limited to, petrolatum and lanolin. Note that both petrolatum and lanolin are available both as a semi-solid and as an oil. See the Merck Index, 11th Ed. Merck & Co., Inc. (1989), which is hereby incorporated by reference. Note that the amounts of the pharmaceutical composition and water to be used are dependent on various factors such as drug dosages and types of hydrocarbonaceous carriers, and in any event, can be determined by a person of ordinary skill in the art without undue experimentation.

Other features and advantages of the invention will be apparent from the following description and from the claims.

DESCRIPTION OF THE PREFERRED EMBODIMENTS

An ophthalmic pharmaceutical composition in accordance with the present invention is mainly comprised of (i) a drug which can be used to treat the eyes, and (ii) a hydrocarbonaceous semi-solid carrier. The semi-solid carrier is a grease, fat or wax-like substance of a pharmaceutical grade, such as petrolatum or lanolin. Other suitable additives, e.g., lecithin, may also be added to the composition.

The drug is selected from relief agents for the dry eye syndrome or other agents for the ocular surface. Namely, nerve-reactivating agents, astringent agents, anti-inflammatory agents, anti-bacterial agents, anti-fungal agents, anti-viral agents, anti-allergic agents, anti-glaucomatous agents, anti-graft rejection agents, or cycloplegic agents.

The aforesaid relief agents for the dry eye syndrome include hydroxy ethyl cellulose, hydroxy propyl methyl cellulose, gelatin, polyvinyl alcohol, vitamin A, and the like. The aforesaid nerve-reactivating agents include vitamin B1, vitamin B2, vitamin B6, vitamin B12, vitamin C, vitamin E, vitamin K, and the like. The aforesaid astringent agents include camphor, menthol, zinc sulfate, naphazoline HCl, tetrahydrozoline, phenylephrine, and the like. The aforesaid anti-inflammatory agents include fluorometholone, prednisolone acetate, dexamethasone alcohol, and the like. The aforesaid anti-bacterial agents include sulphanilamide, neomycin, terramycin, erythromycin, amphotericin B, and the like. The aforesaid anti-viral agents include idoxuridine and the like. The aforesaid anti-allergic agents include antazoline, naphazoline, and the like. The aforesaid anti-glaucomatous agents include pilocarpine, epinephrine, timolol, and the like. The aforesaid anti-graft rejection agents include cyclosporine A and the like. The aforesaid cycloplegic agents include tropicamide, atropine, and the like.

The ophthalmic pharmaceutical composition of this invention is preferably presented in the form of a semi-solid at room temperature. When immersed in water of a temperature above the melting point of the semi-solid, it immediately melts into an oily form. The mixture of the ophthalmic pharmaceutical composition and water can then be conveniently nebulized with a nebulizer by means of ultrasonic vibration. When the composition is dissolved into oily form and nebulized with water, the nebulized fine drops of liquid can then be easily and smoothly delivered to the ocular surface of the patient's eye by gentle currents of air (e.g., provided by a fan installed in the nebulizer).

Without further elaboration, it is believed that one skilled in the art can, based on the description herein, utilize the present invention to its fullest extent. The following specific examples are, therefore, to be construed as merely illustrative, and not limitative of the remainder of the disclosure in any way whatsoever.

EXAMPLE I (for treating dry eye syndrome)
1. Formula-I
   petrolatum: 94 grams
   camphor: 5 grams
   menthol: 1 gram
   Vitamin A: 500000 IU
2. Nebulizing Test About 1 gram of the composition of Formula-I was added to a cup containing 5 g water at 60° C., permitting the composition of Formula-I to melt into an oily form floating on the top of the water. The cup was then placed in a nebulizer (Model 8050, Formosa-CJ Business Corp., Taipei, Taiwan) which nebulized the water-oil mixture in the cup into fine drops of liquid. The temperature of the nebulized fine drops of liquid was about 25° C. Each fine drop of liquid comprised a hydrophilic inner core and a lipophilic outer layer.

EXAMPLE II (for treating chronic conjunctivitis)
1. Formula-II
   petrolatum: 88.98 grams
   camphor: 9 grams
   menthol: 2 grams
   Vitamin B12: 20 milligrams
2. Nebulizing Test About 1 gram of the composition of Formula-II was added to a cup containing 5 g water at 60° C., permitting the composition of Formula-II to melt into an oily form floating on the top of the water. The cup was then placed in a nebulizer (Model 8050, Formosa-CJ Business Corp., Taipei, Taiwan) which nebulized the water-oil mixture in the cup into fine drops of liquid. The temperature of the nebulized fine drops of liquid was about 25° C. Each fine drop of liquid comprised a hydrophilic inner core and a lipophilic outer layer.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of administering a drug to an eye, which method comprises:

(a) admixing a pharmaceutically acceptable hydrocarbonaceous semi-solid or oil which contains the drug with water at a temperature above the melting point of said semi-solid or oil;

(b) nebulizing said admixture to form liquid drops; and (c) applying said liquid drops to the eye.

2. The method of claim 1, wherein said semi-solid or oil is semi-solid.

3. The method of claim 1, wherein said semi-solid or oil is oil.

4. The method of claim 1, wherein said semi-solid or oil is petrolatum.

5. The method of claim 1, wherein said semi-solid or oil is lanolin.

6. The method of claim 1, wherein said semi-solid or oil is a semi-solid which melts at 30°–100° C.

7. The method of claim 1, wherein said drug is selected from the group consisting of a relief agent for the dry eye syndrome, a nerve-reactivating agent, an astringent agent, an anti-inflammatory agent, an anti-bacterial agent, an anti-fungal agent, an anti-viral agent, an anti-allergic agent, and anti-glaucomatous agent, an anti-graft rejection agent, and a cycloplegic agent.

8. The method of claim 7, wherein said semi-solid or oil is selected from the group consisting of petrolatum and lanolin.

9. The method of claim 7, wherein said drug is hydroxy ethyl cellulose, hydroxypropylmethyl cellulose, gelatin, polyvinyl alcohol, vitamin A, vitamin B1, vitamin B2, vitamin B6, vitamin B12, vitamin C, vitamin E, vitamin K, camphor, menthol, zinc sulfate, naphazoline, tetrahydroxoline, phenylephrine, prednisolone acetate, dexamethasone alcohol, sulfanilamide, neomycin, terramycin, erythromycin, gentamicin, amphotericin B, idoxuridine, antazoline, sodium chromoglycate, pilocarpine, epinephrine, timolol, cyclosporine A, tropicamide, or atropine.

* * * * *